United States Patent
Dyer et al.

(10) Patent No.: US 10,625,021 B2
(45) Date of Patent: Apr. 21, 2020

(54) APPARATUS FOR REINFORCING SYRINGE CARTRIDGE

(71) Applicant: Portal Instruments, Inc., Cambridge, MA (US)

(72) Inventors: Robert J. Dyer, Concord, MA (US); Andrew Coats, Somerville, MA (US); Nikolay Lapin, Westwood, MA (US)

(73) Assignee: Portal Instruments, Inc., Cambridge, MA (US)

( * ) Notice: Subject to any disclaimer, the term of this patent is extended or adjusted under 35 U.S.C. 154(b) by 434 days.

(21) Appl. No.: 15/420,185

(22) Filed: Jan. 31, 2017

(65) Prior Publication Data
US 2017/0259000 A1    Sep. 14, 2017

Related U.S. Application Data

(60) Provisional application No. 62/305,569, filed on Mar. 9, 2016.

(51) Int. Cl.
*A61M 5/30* (2006.01)
*A61M 5/24* (2006.01)
*A61M 5/31* (2006.01)

(52) U.S. Cl.
CPC ............... *A61M 5/30* (2013.01); *A61M 5/24* (2013.01); *A61M 5/3129* (2013.01); *A61M 5/3007* (2013.01); *A61M 2005/2407* (2013.01); *A61M 2005/2411* (2013.01); *A61M 2005/2418* (2013.01); *A61M 2005/2477* (2013.01); *A61M 2005/2488* (2013.01); *A61M 2205/02* (2013.01)

(58) Field of Classification Search
CPC .......... A61M 5/24; A61M 5/282; A61M 5/30; A61M 5/3007; A61M 2005/2403; A61M 2005/2433; A61M 2005/2485; A61M 2005/2481; A61M 2005/2407; A61M 2005/2411; A61M 2005/2418; A61M 2005/2477; A61M 2005/2496; A61M 2205/02
USPC ........................................................ 604/323
See application file for complete search history.

(56) References Cited

U.S. PATENT DOCUMENTS

| | | | | |
|---|---|---|---|---|
| 3,110,309 | A | * 11/1963 | Higgins | ............ B05C 17/00586 604/201 |
| 2012/0035542 | A1 | * 2/2012 | Pongprairochana | .... A61M 5/20 604/110 |
| 2013/0085458 | A1 | * 4/2013 | Manke | .................... A61M 5/24 604/228 |
| 2016/0213845 | A1 | 7/2016 | Holmqvist | |

* cited by examiner

*Primary Examiner* — Kevin C Sirmons
*Assistant Examiner* — Tezita Z Watts
(74) *Attorney, Agent, or Firm* — Occhiuti & Rohlicek LLP

(57) ABSTRACT

An apparatus for transdermal injection includes a collet configured to transition between first and second states. In the first state, the collet receives a cartridge with a predetermined elongate shape. In the second state, an inner surface of the collet substantially conforms to the predetermined elongate shape of the cartridge such that expansion of the cartridge, when the cartridge is pressurized, is substantially uniformly opposed.

9 Claims, 15 Drawing Sheets

APPARATUS FOR REINFORCING SYRINGE CARTRIDGE

CROSS REFERENCE TO RELATED APPLICATIONS

This application claims priority to U.S. Provisional Application No. 62/305,569, filed on Mar. 9, 2016, the contents of which are hereby incorporated by reference in their entirety.

FIELD OF INVENTION

This invention relates to delivery of drugs, and in particular, to injecting drugs through the skin.

BACKGROUND

The skin of organisms such as humans serves as a protective barrier that, among other functions, prevents pathogens from entering the body and prevents or regulates fluids such as blood and water from exiting the body. In the field of modern medicine, there is often a need to deliver injectates such as drugs through the skin and into the bloodstream of patients. Traditionally, this delivery of liquids into a patient's body is accomplished by insertion of a needle through the patient's skin and into an area inside of the patient's body where the liquid can enter the patient's blood stream.

However, the use of needles to deliver liquids into a patient's body has a number of significant drawbacks such as the pain associated with being pierced by a needle, the fear that many patients have of needles, and the skin damage and associated risk of infection that occurs due to the use of needles.

As a result, needle-free transdermal injection devices have been developed. These devices use a high pressure, narrow jet of injection liquid or powder to penetrate a patient's skin, obviating the need to pierce the patient's skin with a needle.

One way to deliver a drug is to place it inside a cylinder having a piston at one end thereof, and to drive the piston impulsively to provide the necessary pressure to separate the skin cells. Unfortunately, pressure acts in all directions, and in particular, acts against the wall of the cartridge. This causes the wall to bow outward and/or compress, thus increasing the volume of the cartridge and reducing the overall pressure. This deformation is more likely to occur during periods of rapid acceleration which can lead to imprecise delivery (i.e., incorrect dosage) and even malfunction. The lost injection energy and decrease in acceleration of the injectates can also "wetness" (i.e., residual injectate on the skin).

Increasing the thickness of the wall does not prevent deformation of the inner wall of the cartridge (e.g., bending, buckling, or compression). Even relatively thick glass or medical grade plastic cartridges can compress under certain delivery pressures as those materials are not sufficiently rigid.

SUMMARY

The invention provides a way to reinforce the cartridge so that it can sustain a high pressure impulse with negligible deformation.

In a general aspect, the invention features an apparatus for transdermal injection. Such an apparatus includes a collet configured to transition between first and second states. In the first state, the collet receives a cartridge. In the second state, the collet supports the cartridge. It is noted that the collet described herein does not have all of the properties of a conventional collet and does not necessarily conform to the conventional definition of the term 'collet.' Indeed, the collet described herein holds and substantially uniformly supports a wall of a cartridge to prevent deformation of the wall (e.g., bending, buckling, or compression) when the cartridge is pressurized; a function which is not performed by conventional collets. Indeed, conventional collets are often segmented metal bands, collars, ferrules, or flanges which use friction to hold a tool (e.g., a drill bit) in place. In operation, the segments of a conventional collet are never fully closed and therefore conventional collets are incapable of substantially uniformly supporting a wall of a cartridge to prevent deformation of the wall.

In some embodiments, the collet comprises first and second legs, each of which has an inner surface that defines a recess that conforms to a cartridge. The two legs pivot during transition of the collet between its two states. Among these embodiments are those in which the recess accommodates a frustoconical surface. Also among these embodiments are those in that include pivots inserted through distal ends of the legs, those in which the legs each comprise a straight proximal section and a tapered distal section, those in which the legs drive a cartridge distally direction as the collet transitions from the first to the second state, those in which, when the collet is in its second state, the recesses of the first and second leg collectively support every point on an outer wall of the cartridge, and those in which fingers move along lines parallel to an axis of the collet and cause the transition as they do so. Among these embodiments with fingers are those in which, as the fingers climb the legs, the collet transitions into the second state.

Yet other embodiments include fingers that move along lines parallel to an axis of the collet. In these embodiments, the fingers cause the transition as they move.

Some embodiments include a yoke, with fingers for engaging legs of the collet being constituents of this yoke.

Also among the embodiments are those in which, when the collet is in the second state, the cartridge is flush with a distal end of the collet.

In another general aspect, a method for carrying out a transdermal injection includes loading a cartridge having a predetermined elongate shape into a collet which defines a chamber for supporting an injectable material, causing the collet to transition into a state in which the collet substantially conforms to the predetermined elongate shape of the cartridge such that, upon pressurization of the cartridge, expansion of the cartridge is substantially uniformly opposed, and applying pressure at a proximal end of the cartridge, thereby pressurizing the cartridge and causing ejection of the injectable material from a distal end of the cartridge.

Aspects may include one or more of the following features.

The collet may include first and second legs, the legs each having an inner surface that defines a recess configured to substantially conform to the predetermined elongate shape of the cartridge. The first and second legs may be configured to pivot during transition of the collet between the first and second states. Causing the collet to transition in to the state in which the collet supports substantially all points on the outer wall of the cartridge may include moving fingers along an outer surface of the collet in a direction parallel to an axis of the collet, thereby causing the legs to pivot into the state.

A ratio of a length of the cartridge to the width of the cartridge may be 10 to 1. A ratio of a length of the cartridge to the width of the cartridge may be 50 to 1. The cartridge may include an outer wall and an inner wall, and in the state the collet may support substantially all points on the outer wall of the cartridge. A distance between the outer wall of the cartridge and the inner wall of the cartridge may be in a range of 0.5 mm to 6 mm. The predefined shape of the cartridge may be a substantially frustoconical shape.

In another general aspect, a method for carrying out a transdermal injection includes the following steps. A cartridge is loaded into a collet, the cartridge having an outer wall and an inner wall, which defines a chamber for supporting an injectable material. The collet is caused to transition into a state in which the collet supports all points on the outer wall of the cartridge. An impulse of pressure is applied at a proximal end of the cartridge, thereby causing ejection of the injectable material from a distal end of said cartridge.

In yet another general aspect, an apparatus for transdermal injection includes a sleeve including a proximal end, a distal end, and an inner wall surface extending along the sleeve from a first opening at the proximal end to a second opening at the distal end. The inner wall surface forms a channel in the sleeve, the channel having a first portion with a substantially frustoconical shape. The channel of the sleeve is configured to receive a substantially frustoconically shaped injection cartridge, to substantially uniformly support the injection cartridge during a transdermal injection operation, and to prevent movement of the injection cartridge out of the distal end of the sleeve.

Aspects may include one or more of the following features.

The sleeve may include a stop edge disposed at the distal end, the stop edge being configured to prevent movement of the injection cartridge out of the distal end of the sleeve. The channel may include a second portion extending from the second opening to the first portion of the channel, the second portion having a substantially cylindrical shape. The sleeve may include a ring disposed in the second portion of the channel, the ring having a hole with a first inner diameter smaller than a second inner diameter of a distal end of the first portion of the channel and forming the stop edge at a point in the channel where the first portion and the second portion meet.

The ring may be press fit into the second portion of the channel. The ring may be welded into the second portion of the channel. The ring may be fixed in the second portion of the channel using an adhesive. A portion of an outer wall surface adjacent to the sleeve proximal end may include threads. A diameter of the first portion of the channel may taper from a first diameter in a range of 7 mm to 8 mm to a second diameter in a range of 6 mm to 7 mm.

A thickness of a wall of the sleeve adjacent to the first portion of the channel may be in a range of 0.5 mm to 5 mm. The sleeve may be formed from a stainless steel material.

In yet another general aspect, an apparatus for transdermal injection includes a cartridge including a proximal end, a distal end, an outer wall surface, an inner wall surface, and an injection nozzle disposed at the distal end of the cartridge. The outer wall surface extends between the proximal end and the distal end and has a substantially frustoconical shape. The inner wall surface extends from a first opening at the proximal end and in a direction from the proximal end to the distal end and forms a channel in the cartridge. The channel has a first portion with a substantially cylindrical shape and a second portion with the injection nozzle disposed therein.

Aspects may include one or more of the following features.

The second portion may be configured to receive the injection nozzle and may include a stop edge configured to prevent the injection nozzle from exiting the cartridge from the distal end. The injection nozzle may be affixed in the second portion using an adhesive. The injection nozzle may be affixed in the second portion using a welding technique. The injection nozzle may be integrally formed in the second portion.

The cartridge may include a plunger disposed in the first portion of the channel. A diameter of the outer wall surface may taper from a first diameter in a range of 7.5 mm to 8 mm to a second diameter in a range of 6 mm to 6.5 mm. A thickness of a wall of the cartridge along the first portion of the channel may be in a range of 0.05 mm to 6 mm. The cartridge may be formed from a plastic material. The apparatus may include a Luer connector disposed at the distal end.

In yet another general aspect, an apparatus for transdermal injection includes a sleeve including a sleeve proximal end, a sleeve distal end, and a sleeve inner wall surface extending along the sleeve from a first opening at the sleeve proximal end to a second opening at the sleeve distal end. The sleeve inner wall surface forms a channel in the sleeve, the channel having a first portion with a substantially frustoconical shape. The apparatus also includes a cartridge for insertion into the channel of the sleeve. The cartridge includes a cartridge proximal end, a cartridge distal end, and a cartridge outer wall surface extending between the cartridge proximal end and the cartridge distal end. The cartridge outer wall surface has a substantially frustoconical shape conforming to the first portion of the channel. The sleeve inner wall surface is configured to substantially uniformly support the cartridge outer wall surface during an injection operation.

BRIEF DESCRIPTION OF THE FIGURES

These and other features and advantages of the invention will be apparent from the following detailed description and the accompanying figures, in which.

DETAILED DESCRIPTION

I. First Embodiment

Figure 1A:
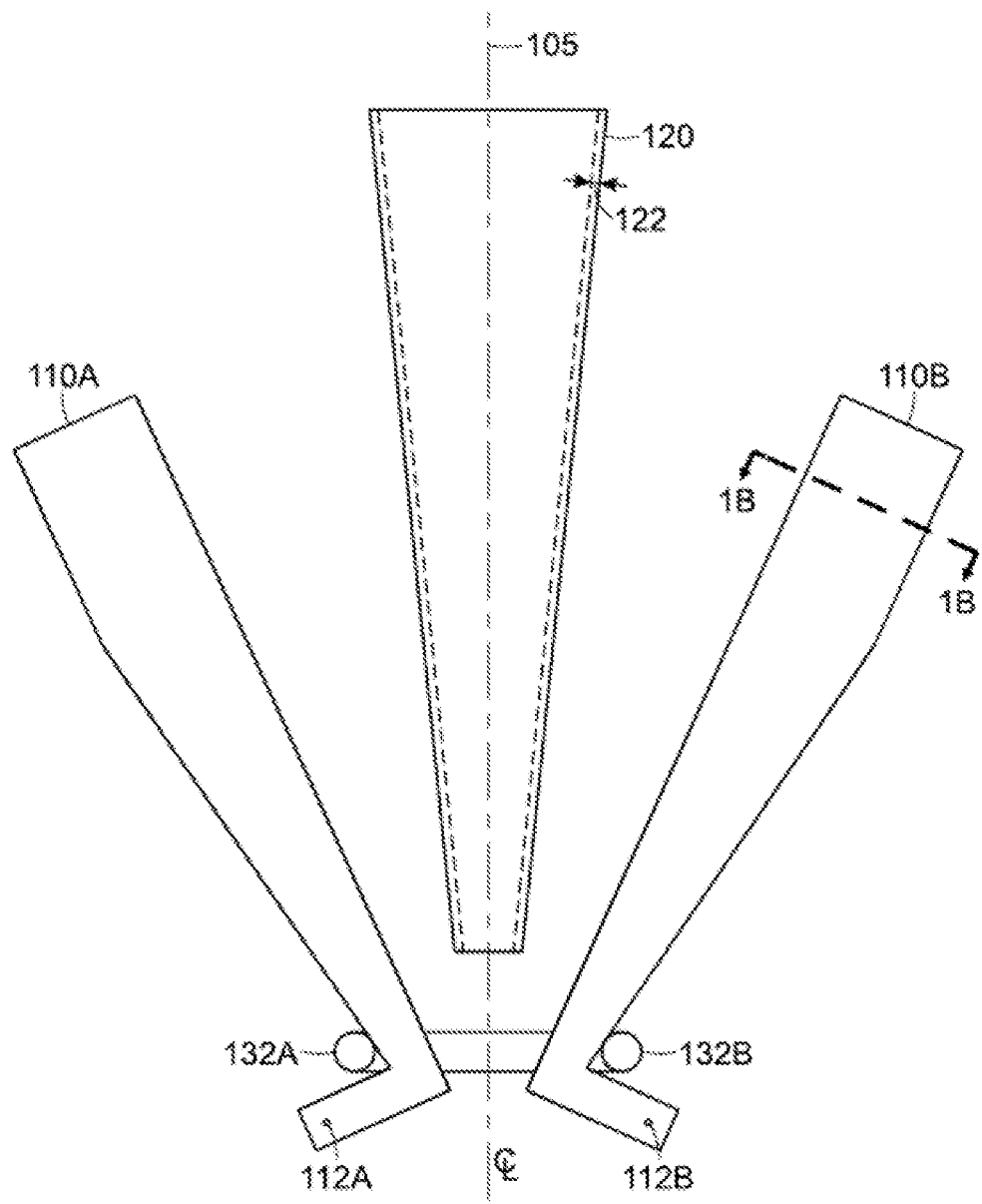
FIG. 1A shows a first embodiment of an injection apparatus in a fully open position for receiving a cartridge.

As shown in FIG. 1A, an apparatus for transdermal injection includes a cartridge 120 for holding an injectable substance (e.g., drug) to be delivered through the skin. The cartridge has a wall 122 having a proximal end and a distal end, with the proximal end being wider than the distal end. Between the proximal and distal end, the wall 122 defines an approximately frustoconical section about an axis 105. The proximal end receives a piston for delivering a pressure impulse and the distal end is placed against the patient's skin.

For purposes of discussion, it is useful to define a cylindrical coordinate system and to define first and second sections of the cartridge 120. A first section is the set of points that are on the outer surface of the cartridge 120 and that have a circumferential coordinate between 0° and 180°. A second section is the set of points on the outer surface of the cartridge 120 that are not in the first set of points.

The apparatus further includes a collet having a first leg 110B and a second leg 110A.

Figure 4A:
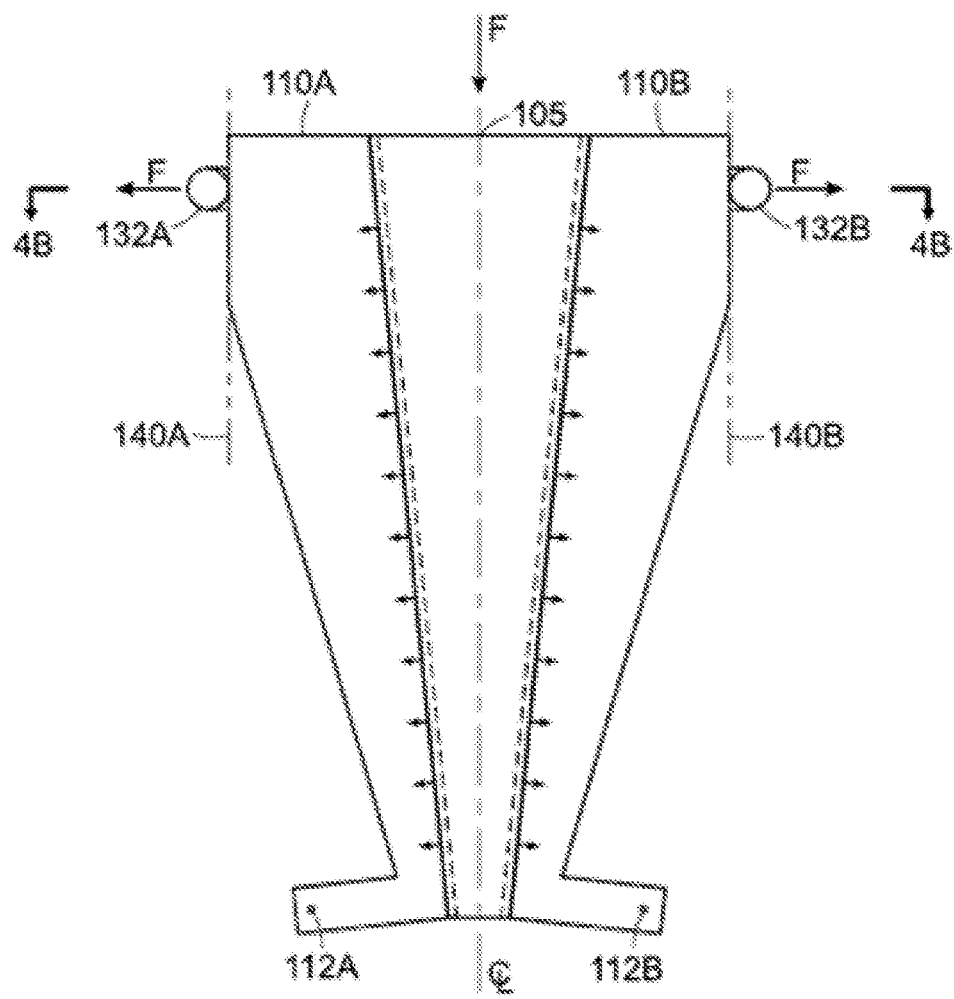
FIG. 4A shows the apparatus of FIG. 1A when the legs are in the fully closed position.

The first leg 110B has a proximal end and a distal end. A first pivot point 112B passes through a foot at the distal end of the first leg 110B. As a result, the first leg 110B can pivot between an open position, as shown in FIG. 1A, and a closed position, as shown in FIG. 4A.

Between its proximal and distal ends, the first leg 110B has an outer surface that defines a straight section and a tapered section. The straight section is that portion of the first leg 110B for which the outer surface is parallel to the axis 105 when the first leg 110B is in the closed position shown in FIG. 4A. The tapered section is one in which the outer surface defines a line that slopes toward the axis 105 so that the outer surface is closest to the axis 105 at the distal end of the first leg 110B and furthest from the axis at the proximal end of the first leg 110B.

The first leg 110B engages a vertically-moving first finger 132B that moves along a line parallel to the axis 105. When the first leg 110B is in its open position, as shown in FIG. 1A, the first finger 132B engages the distalmost portion of the first leg's tapered section. When the first leg 110B is in its closed position, as shown in FIG. 4A, the first finger 132B engages the proximal end of the first leg 110B. It is apparent therefore that as the first finger 132B moves from the distal end to the proximal end, it causes the first leg 110B to pivot counter-clockwise.

Figure 1B:
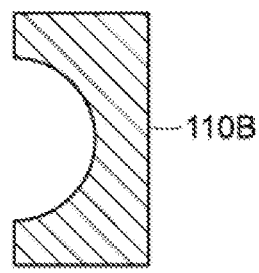
FIG. 1B shows a cross section of a leg of the apparatus of FIG. 1A.

Referring now to FIG. 1B, the first leg 110B has a cross section that features a recess. This recess is shaped to conform exactly to the frustoconical shape of the cartridge 120. As a result, when the first leg 110A is in the fully closed position shown in FIG. 4B, the cartridge is fully nestled within the recess so that the recess supports all points in the first section of the cartridge 120.

The collet's a second leg 110A has a proximal end and a distal end. A second pivot point 112A passes through a foot at the distal end of the second leg 110A. As a result, the second leg 110A can pivot between an open position, as shown in FIG. 1A, and a closed position, as shown in FIG. 4A.

Between its proximal and distal ends, the second leg 110A has an outer surface that defines a straight section and a tapered section. The straight section is that portion of the second leg 110A for which the outer surface is parallel to the axis 105 when the second leg 110A is in the closed position shown in FIG. 4A. The tapered section is one in which the outer surface defines a line that slopes toward the axis 105 so that the outer surface is closest to the axis 105 at the distal end of the second leg 110A and furthest from the axis at the proximal end of the second leg 110A.

The second leg 110A engages a second vertically-moving second finger 132A that moves along a line parallel to the axis 105. When the second leg 110A is in its open position, as shown in FIG. 1A, the second finger 132A engages the distalmost portion of the second leg's tapered section. When the second leg 110A is in its closed position, as shown in FIG. 4A, the second finger 132A engages the proximal end of the second leg 110A. It is apparent therefore that as the second finger 132A moves from the distal end to the proximal end, it causes the second leg 110A to pivot clockwise.

Referring now to FIG. 1B, the second leg 110A has a cross section that features a recess. This recess is shaped to conform exactly to the frustoconical shape of the cartridge 120. As a result, when the second leg 110A is in the fully closed position shown in FIG. 4B, the cartridge is fully nestled within the recess so that the recess supports all points in the second section of the cartridge 120.

Figure 4B:
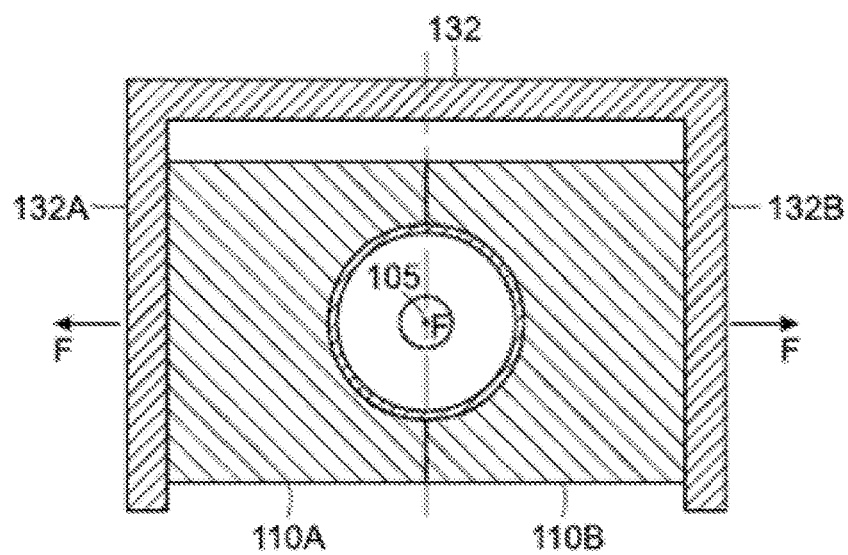
FIG. 4B shows a cross-section of the apparatus when the legs are in the fully closed position as shown in FIG. 4A.

It is apparent therefore that when the first and second legs 110A, 110B are in the fully closed position as shown in FIG. 4A, the entire surface of the cartridge 120 is fully supported, as shown in FIG. 4B. As a result, when a pressure impulse is applied, deformation and/or compression of the walls of cartridge 120 are minimized.

In some embodiments, as shown in FIG. 4B, the first and second fingers 132B, 132A are arms of a single yoke 132 that travels along a path 140A, 140B (FIGS. 3A, 4A, 5, 6) parallel to the axis 105. This is particularly advantageous since the fingers 132B, 132A will inherently be moved together.

A particular advantage of having a leg with both a straight section and a tapered section is that once the fingers 132A, 132B are on the straight section, a distally directed force as shown in FIG. 4A will have no effect on the fingers 132A, 132B. In contrast, had the tapered section continued all the way to the proximal end of the leg 110A, 110B so that there is no straight section, then a distally directed force could be resolved into a component that would tend to force the fingers 132A, 132B distally.

Figure 2A:
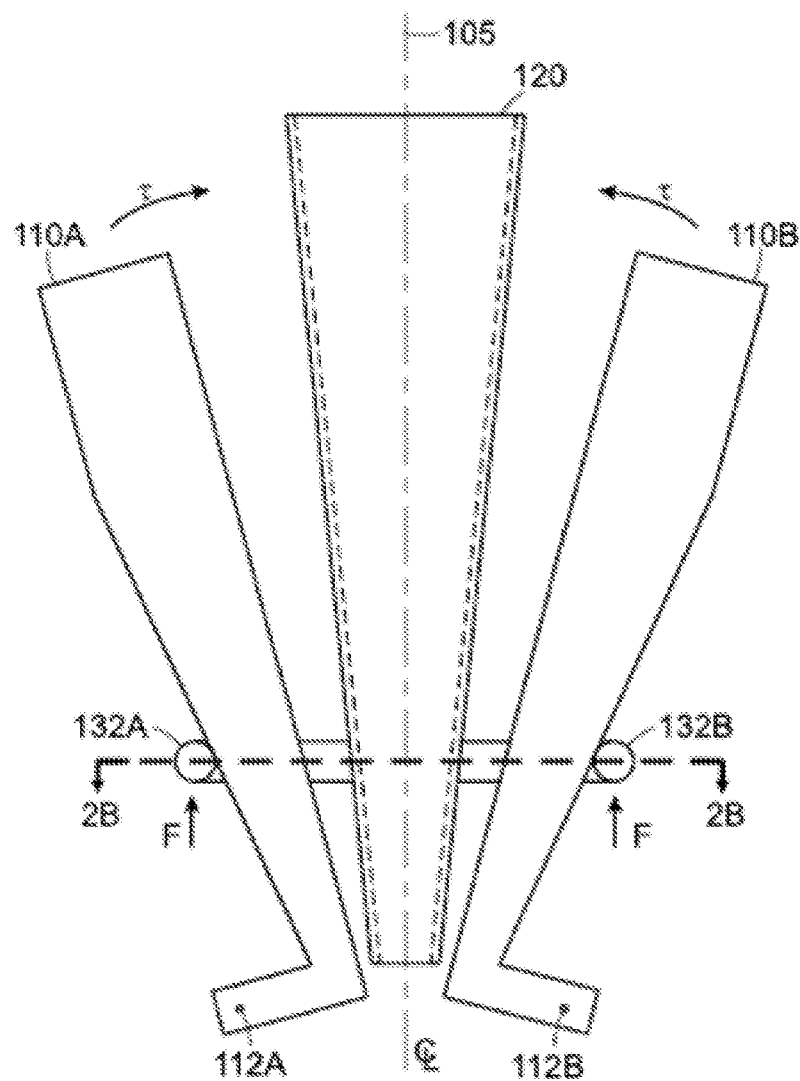
FIG. 2A shows the apparatus of FIG. 1A in an intermediate position with the fingers having climbed part way up the leg.
Figure 2B:
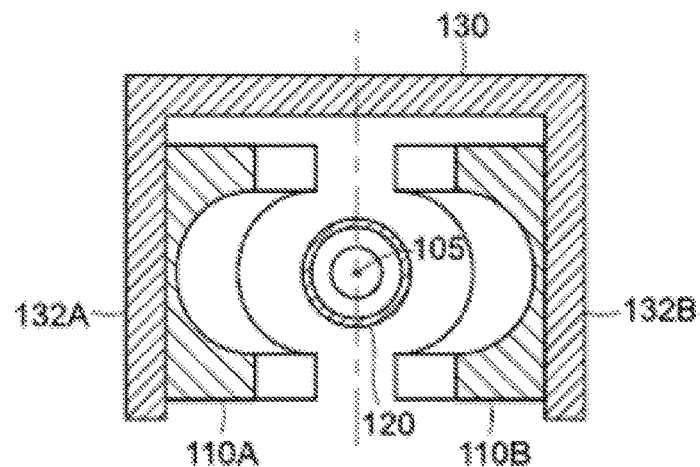
FIG. 2B shows a cross-section of the apparatus when the fingers have climbed to the position shown in FIG. 2A.

As shown in FIG. 4A, the distal tip of the cartridge is flush with the distal tips of the legs 110A, 110B so that it can contact the skin of the patient. This state is reached gradually as the fingers 132A, 132B are moved towards the proximal end of the legs 110A, 110B. As shown in FIG. 2A, with the legs part way up to the straight section, the cartridge 120 is considerably more distal than it was in FIG. 1A. FIG. 2B is a cross section showing that a considerable air gap remains between the cartridge 120 and the walls of the recesses.

Figure 3A:
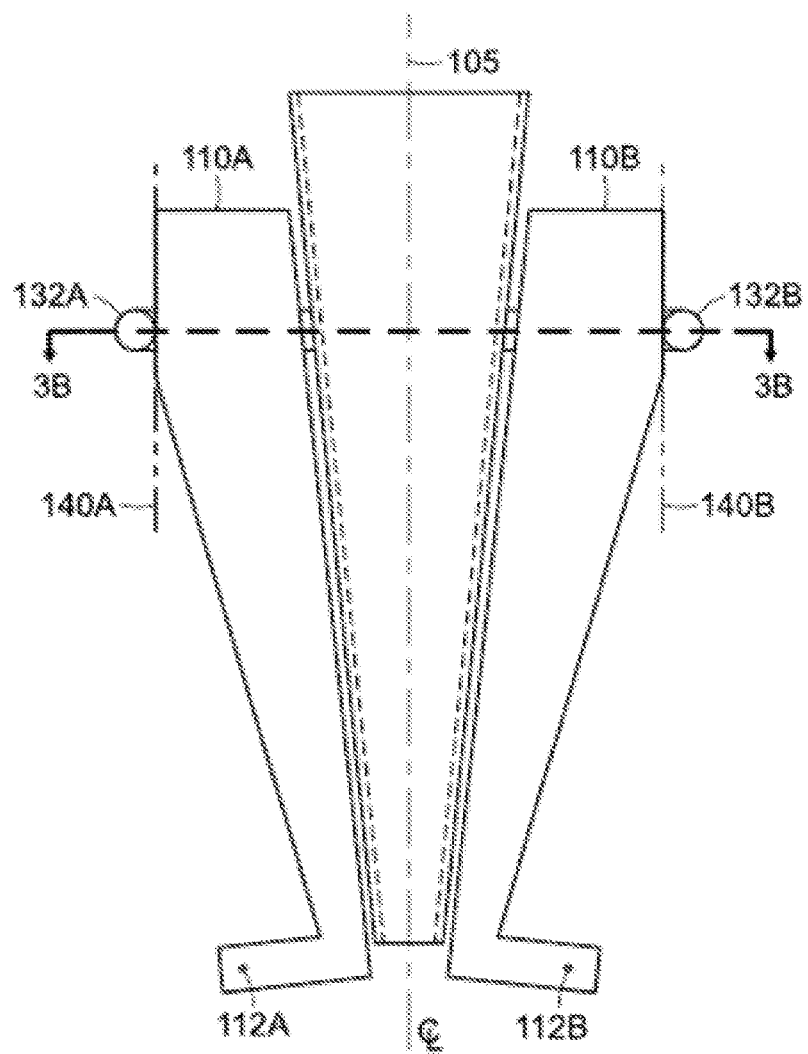
FIG. 3A shows the apparatus of FIG. 1A when the fingers have just reached the straight section of the leg.
Figure 3B:
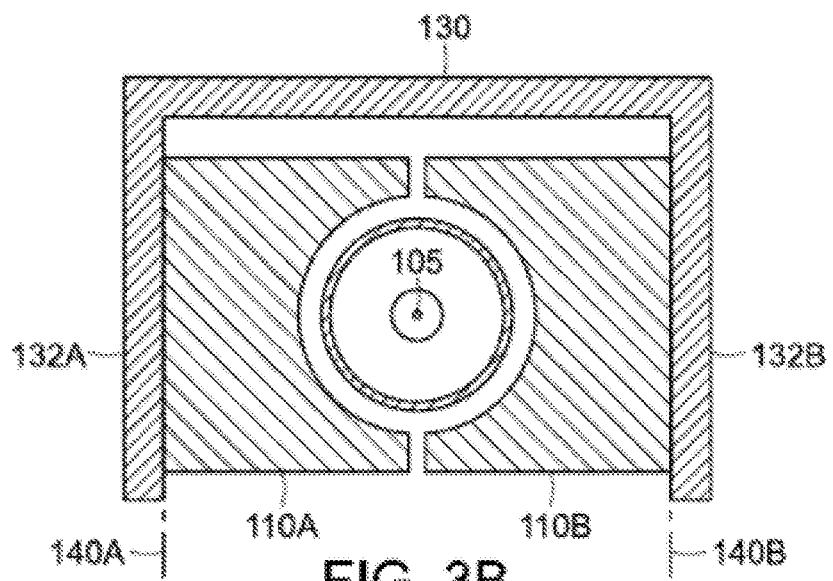
FIG. 3B shows a cross-section of the apparatus when the fingers are positioned as shown in FIG. 3A.

In FIG. 3A, the fingers 132A, 132B have moved all the way to the beginning of the legs' straight sections. In this position, the first and second legs 110A, 110B have now made contact at the level of the fingers 132A, 132B as shown in FIG. 3B. However, the distal tip of the cartridge 120 is not yet aligned with the distal tips of the legs 110A, 110B.

As the fingers 132A, 132B move further in the distal direction, the legs 110A, 110B continue to force the cartridge 120 in the distal direction. By the time the fingers 132A, 132B have reached the top of the straight section, the distal end of the cartridge 120 will have become aligned with the distal end of the legs 110A, 110B so that an injection can be given.

Fingers 132A, 132B can be moved manually or by an actuator (e.g., motor).

The cartridge may be made of a plastic, glass or metal. For example, the cartridge is made of a medical-grade plastic having a thin wall and a flange. In another embodiment, the cartridge is in the form of an ampoule having a wall thickness in a range between 0.05 mm and 6 mm In the embodiment described above in conjunction with FIGS. 1A through 4B, legs having tapered surfaces were used with a counterpart tapered cartridge. Other mechanisms for engaging and providing reinforcing support for the cartridge are also applicable including retention clips, surface grips, interlocking interfaces and tension devices can be used.

II. Second Embodiment

Figure 5:
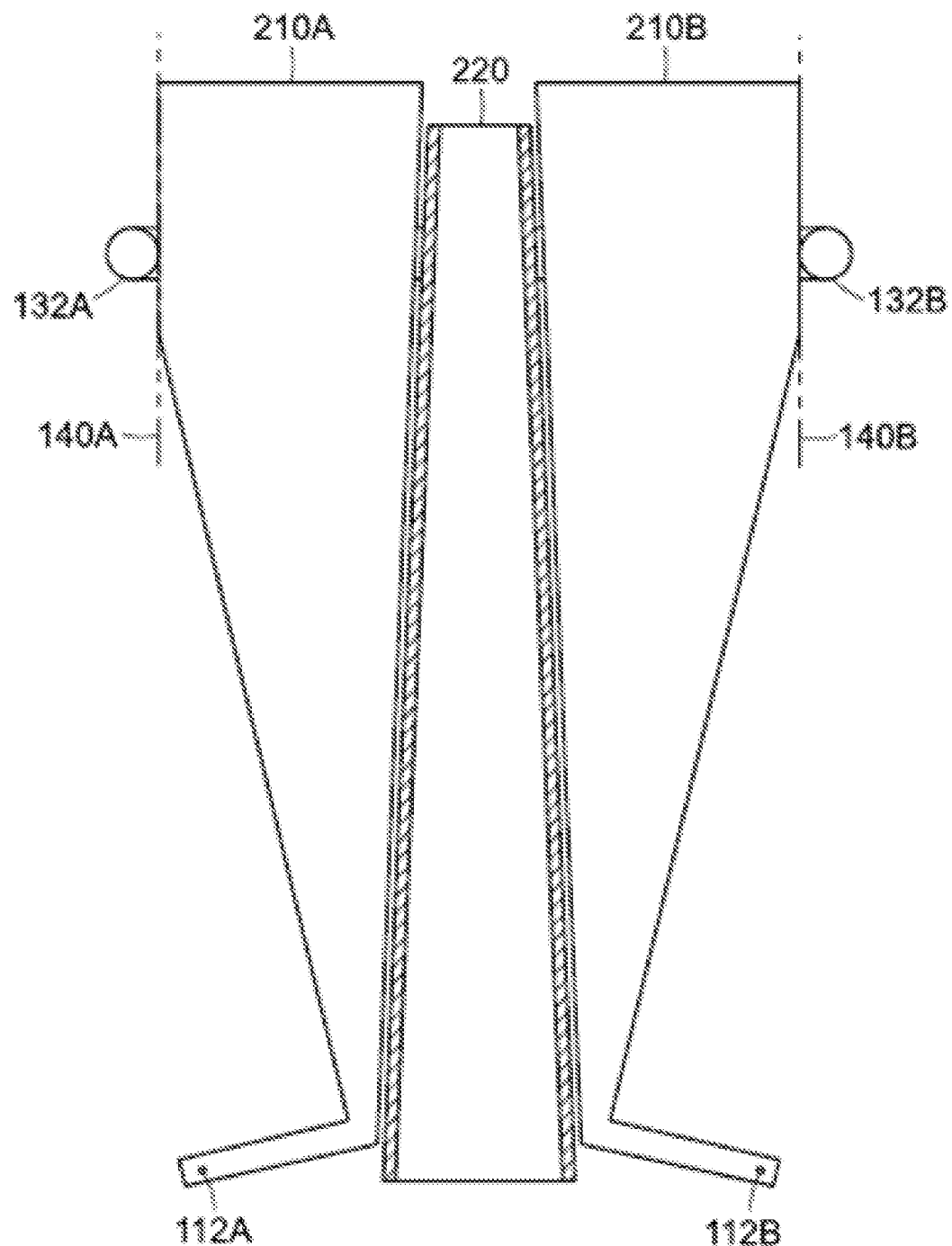
FIG. 5 shows a cross-section of a second embodiment in a fully closed position, generally corresponding to FIG. 3A.
Figure 6:
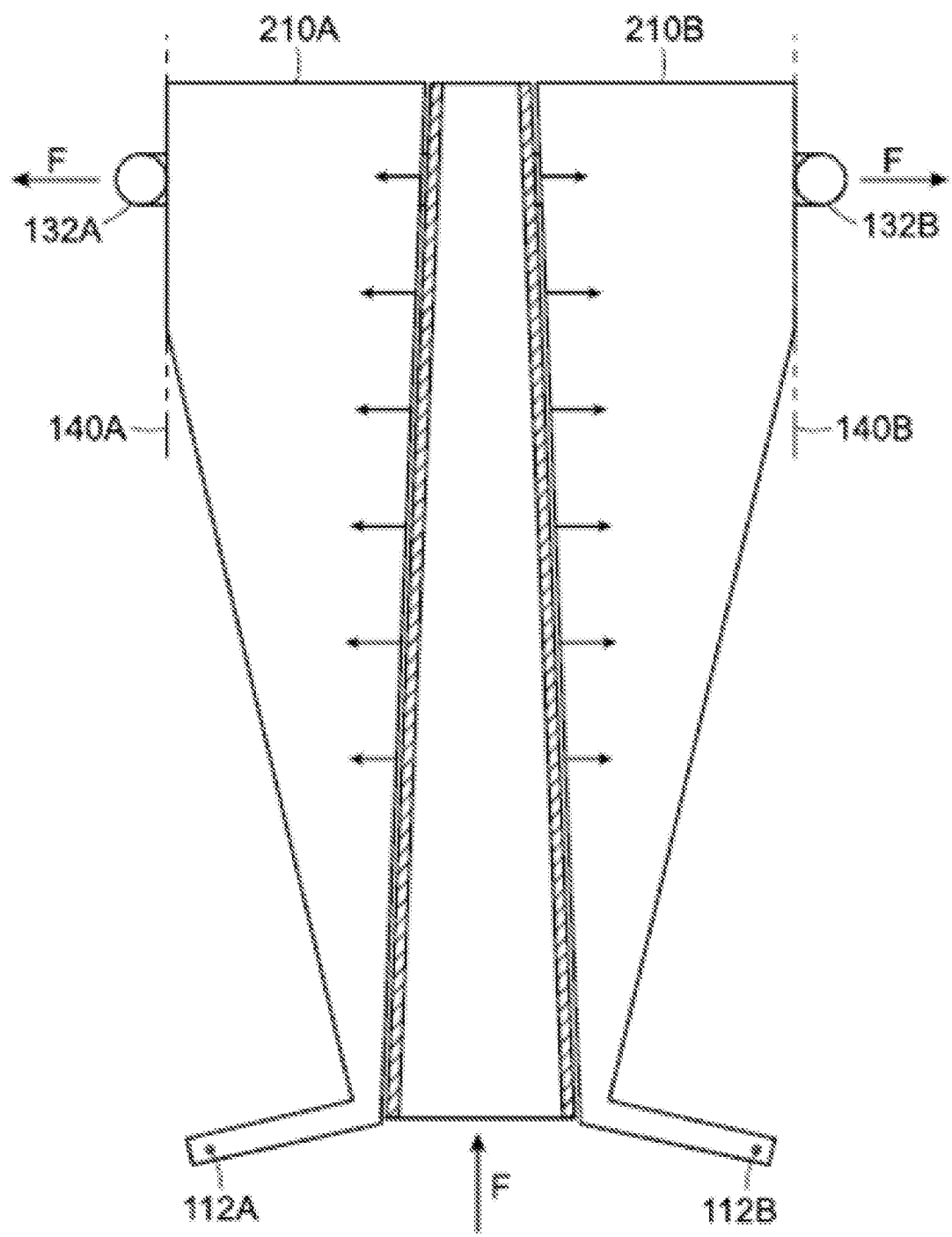
FIG. 6 shows a cross-section of the second embodiment of FIG. 5 in the fully closed position with the cartridge being forced in a direction away from the pivots 112A-B.

Another embodiment is illustrated in FIGS. 5-10. Generally, in the embodiment of FIGS. 1A-4B, the cartridge is inserted in one direction as shown in FIGS. 1A-3A, and then forced in the same direction as shown in FIG. 4A. In this other embodiment, the cartridge is inserted in one direction, as shown in FIG. 5, but then forced in the direction opposite, as shown in FIG. 6. Therefore, the direction of the taper of the cartridge 220 of FIGS. 5-10 is opposite to the direction of taper of cartridge 110 of FIGS. 1A-4B. Similarly, the corresponding taper on the legs 210A-B is opposite to the taper on the legs 110A-B.

III. Third Embodiment

Figure 7:
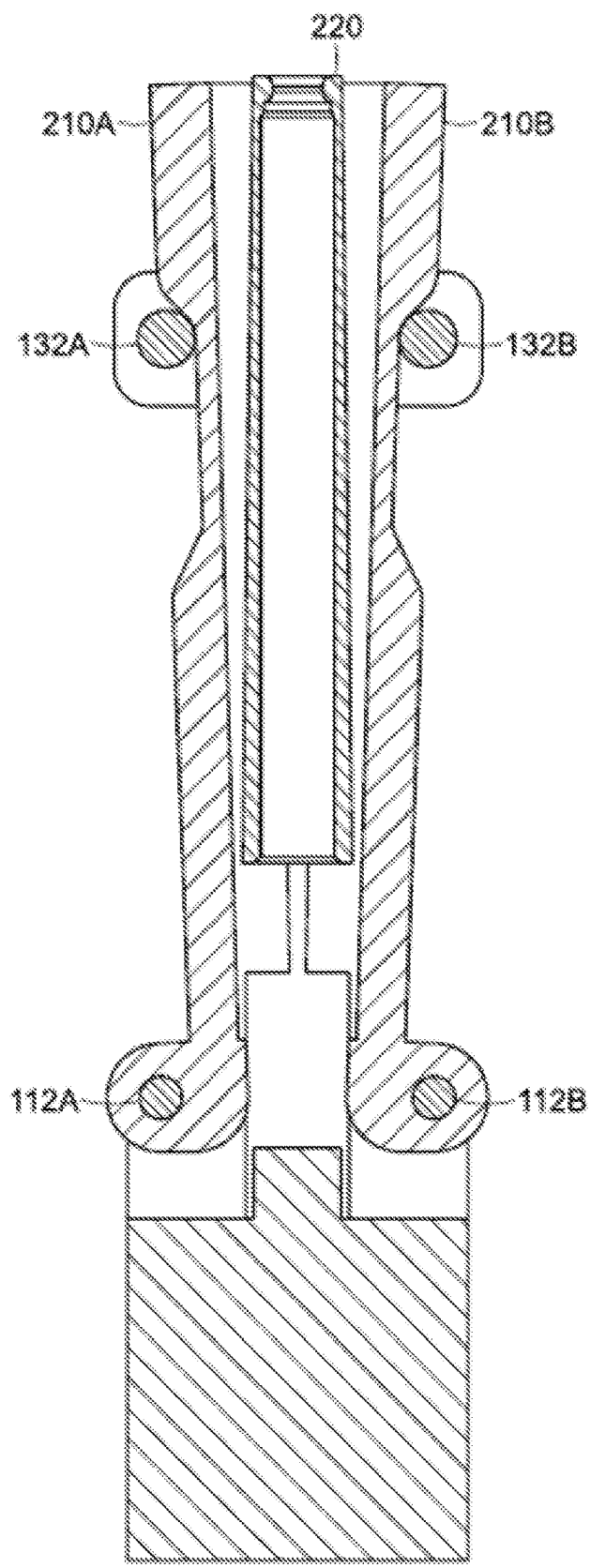
FIG. 7 is a cross-section of a third embodiment, shown in a partially closed position.
Figure 8:
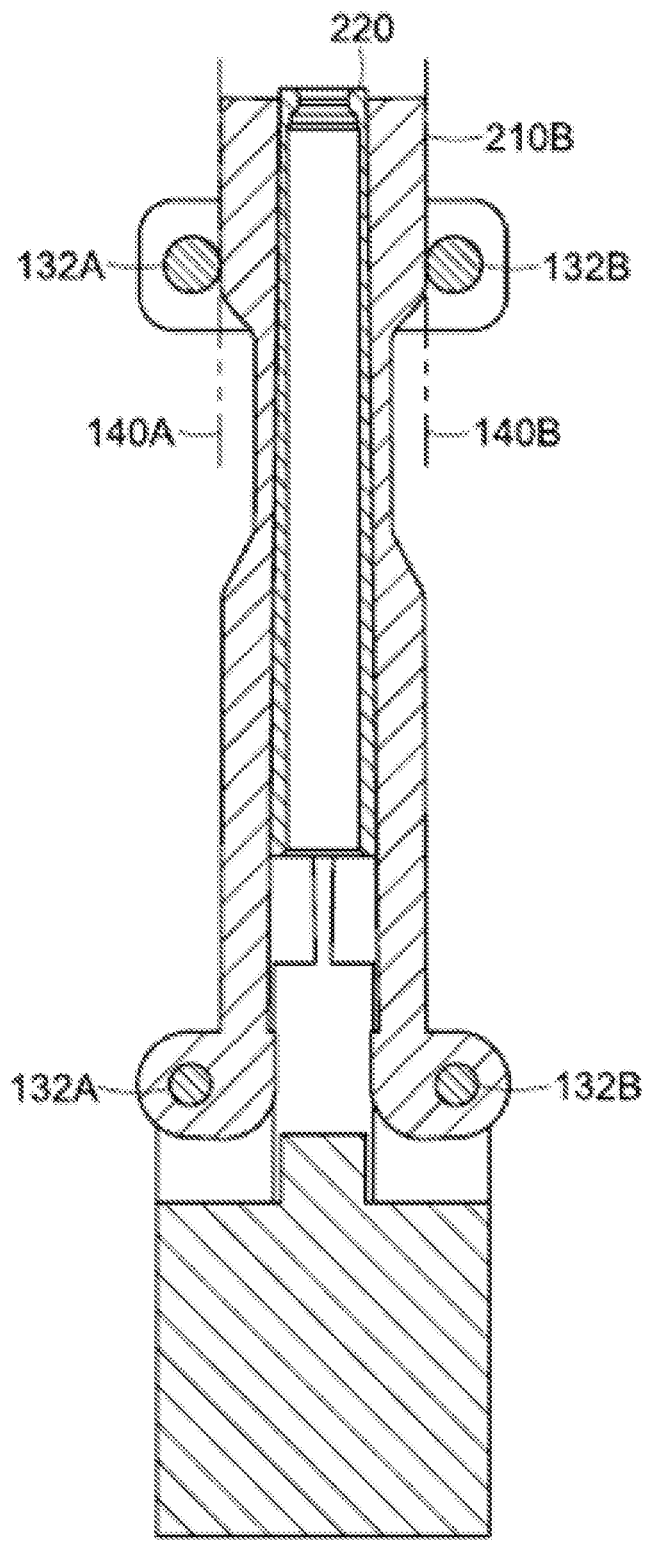
FIG. 8 is a cross-section of the embodiment of FIG. 6, in the closed position.
Figure 9:
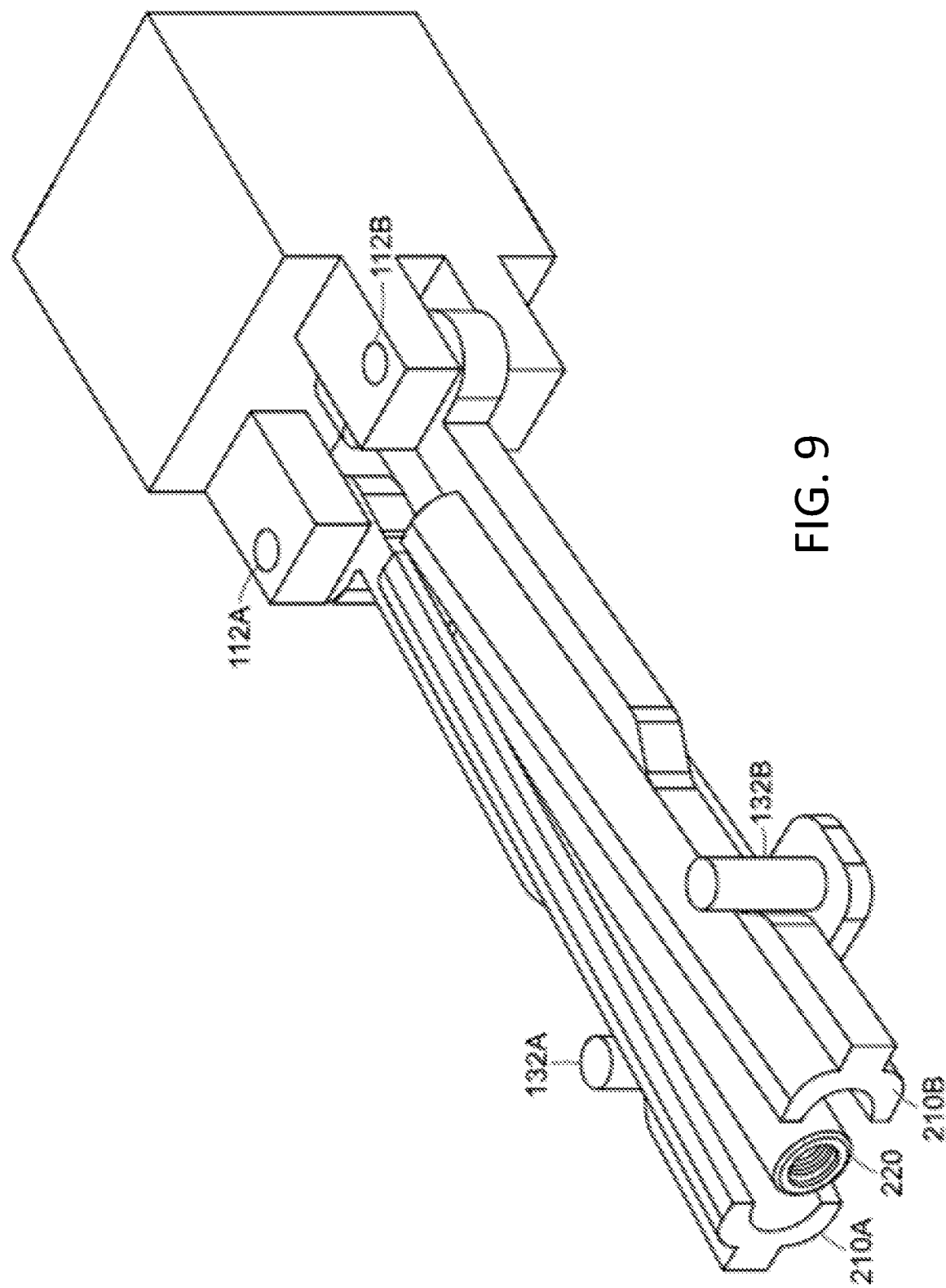
FIG. 9 is a perspective view of the third embodiment in a partially open position corresponding to FIG. 7.
Figure 10:
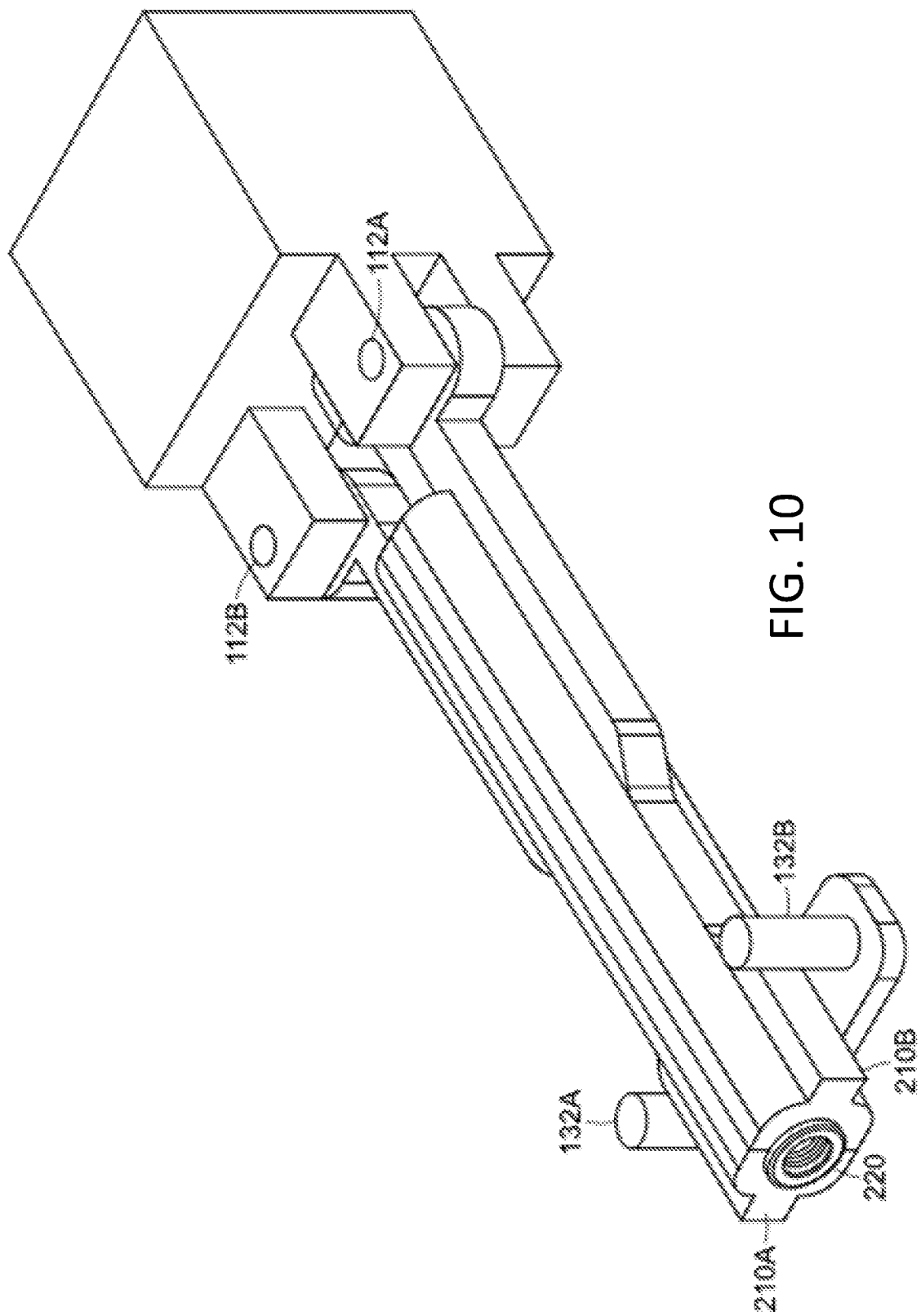
FIG. 10 is a perspective view of the third embodiment in a fully closed position corresponding to FIG. 8.

FIGS. 7-10 show another version of the embodiment of FIGS. 5-6, with the elements labeled with same reference numerals to show the correspondence of the parts. FIGS. 7 and 9 show this version in a partially open position, and FIGS. 8 and 10 show this version in the closed position.

A preliminary study was conducted to investigate the effect of supporting a thin-walled plastic cartridge with a collet on cartridge deformation, compared to the deformation of a thick-walled stainless steel cartridge. Three cartridges were subjected to an increasing load ranging from 100 N to 700 N and the output cartridge deformation (mm) was recorded.

Figure 11:
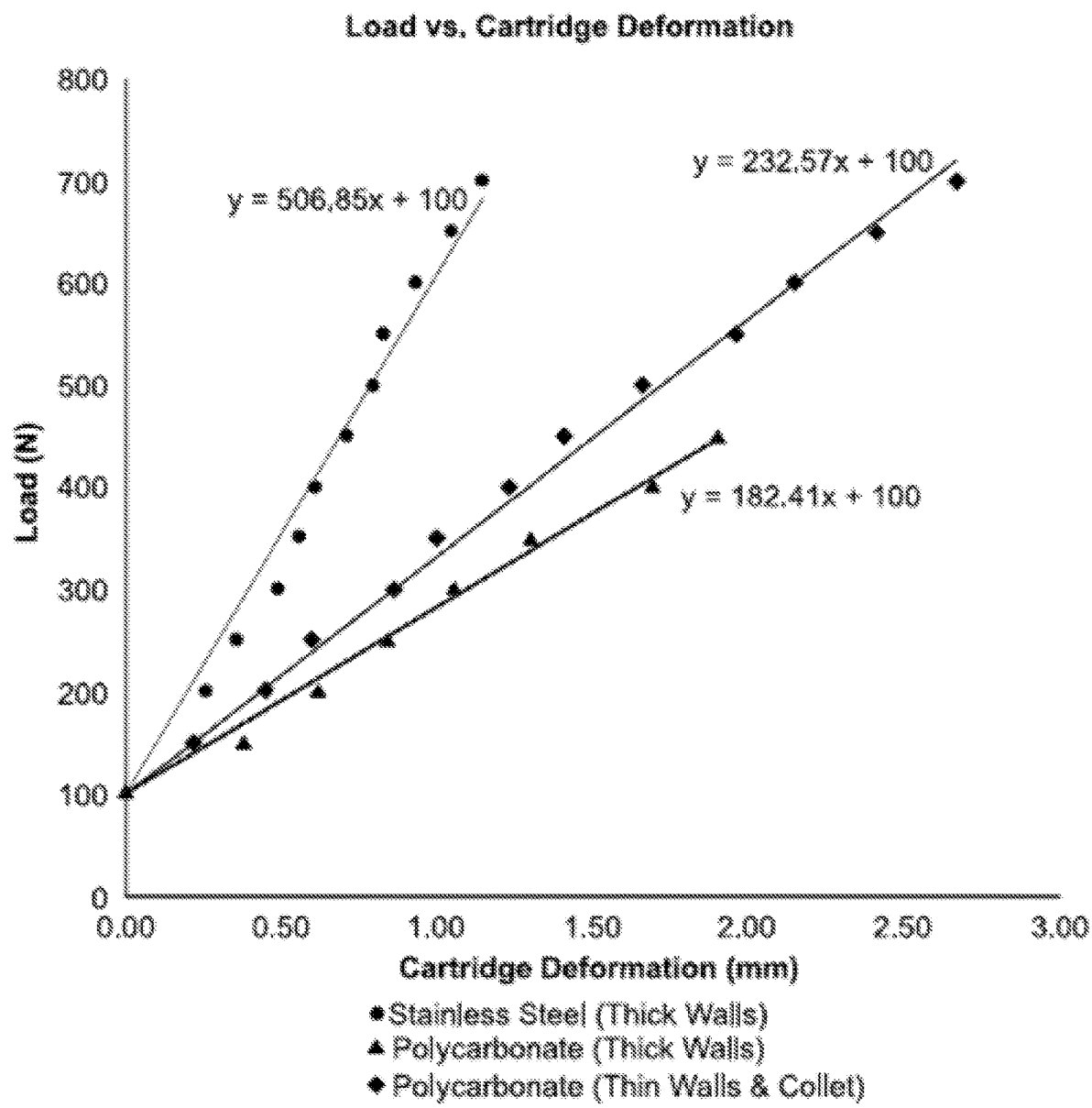
FIG. 11 is representative data showing load versus cartridge deformation for a thin-walled plastic cartridge with a collet as well as for a thick-walled stainless steel cartridge.

Referring to FIG. 11, the data shows increased compliance in an uncolleted thick-walled polycarbonate cartridge, compared to an uncolleted thick-walled stainless steel cartridge, and a decrease in cartridge compliance of a thin-walled polycarbonate cartridge upon the addition of a supporting collet. It should be understood that there are numerous other alternative embodiments. For example, rather than 2 legs, N>2 (e.g., 3, 4, etc.) legs may be used to hold the cartridge. Also, various methods of mechanically biasing or forcing the legs to the closed position may be used. For example, the pivots 132A-B may have torsional springs coupled to them to bias the legs. In some embodiments, the force that pushes the cartridge along or opposite to the direction of insertion (e.g., as shown in FIGS. 4A and 6) may result while applying pressure to the fluid in the cartridge during the process of expelling the fluid from the cartridge. For example, in FIG. 4, force may be applied to pressurize the fluid via the end of the cartridge distant from the pivots 112A-B, and fluid expelled at the end of the pivots, and this force causes the taper of the cartridge 120 to engage the taper of the legs 110A-B. As another example, in FIG. 6, force to pressurize the fluid is applied at the end of the cartridge 220 near the pivots 112A-B, and the fluid is ejected at the other end of the cartridge, and this force causes the cartridge to engage the taper of the legs 210A-B.

IV. Fourth Embodiment

Figure 12:
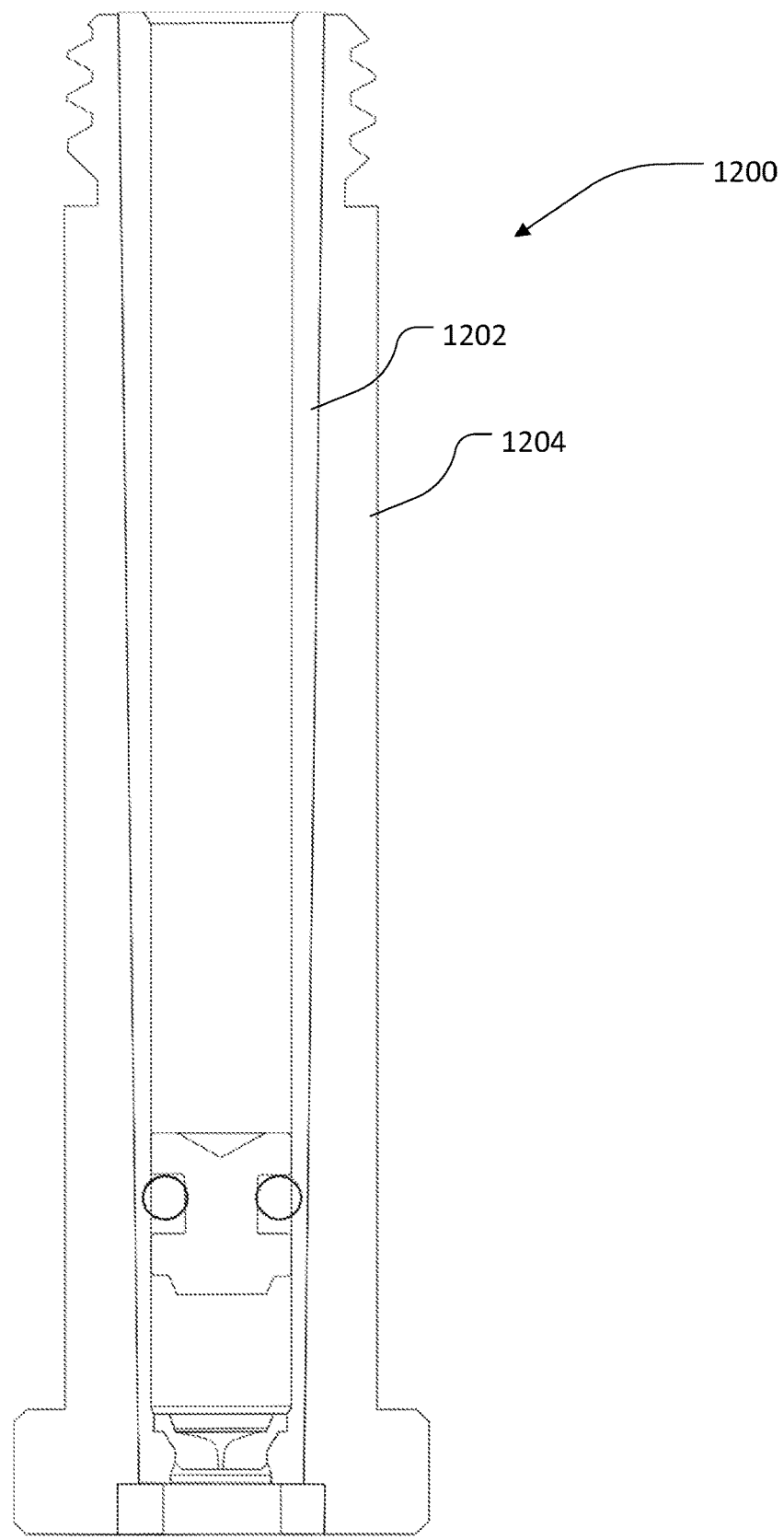
FIG. 12 is a fourth embodiment in an assembled state.

Referring to FIG. 12, in another embodiment, an injector head assembly 1200 includes a cartridge 1202 inserted into a reinforcing sleeve 1204. The cartridge 1202 is configured to hold an injectate for delivery through a patient's skin. The cartridge 1202 has a relatively thin walls which are susceptible to deformation (e.g., ballooning) when the injectate in the cartridge 1202 is pressurized. The reinforcing sleeve 1204 is a rigid member configured to receive and support the cartridge 1202 such that deformation of the cartridge 1202 is substantially prevented during an injection operation.

a. Reinforcing Sleeve

Figure 13:
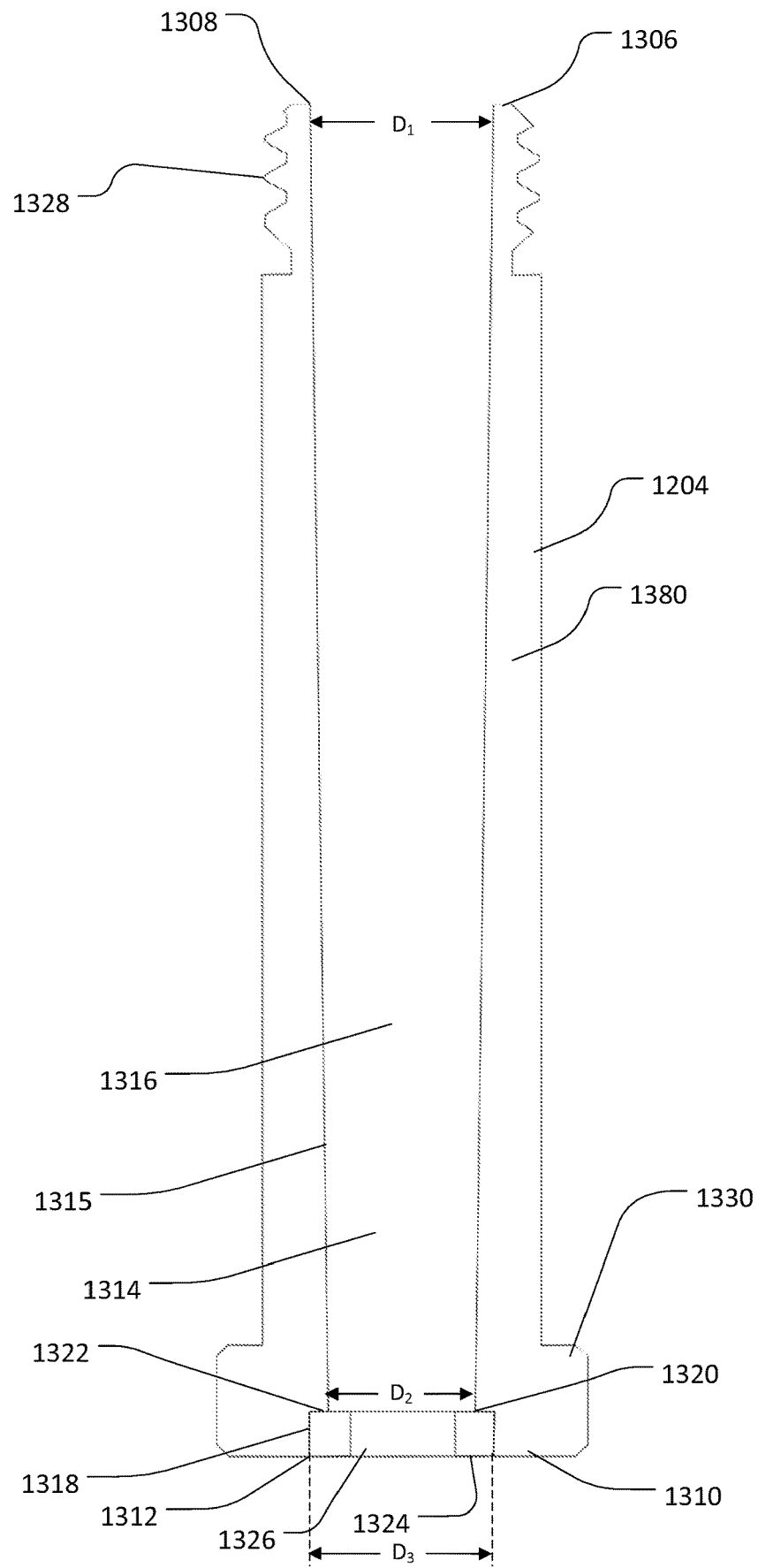
FIG. 13 is a reinforcing sleeve of the fourth embodiment of FIG. 12.

Referring to FIG. 13, the reinforcing sleeve 1202 is an elongate, substantially cylindrical member formed from a rigid material such as stainless steel. The reinforcing sleeve 1204 has a sleeve proximal end 1306 having a sleeve proximal end opening 1308 and a sleeve distal end 1310 having a sleeve distal end opening 1312. A first channel 1314 is defined by an inner surface 1315 of the reinforcing sleeve 1204 and extends along a length of the reinforcing sleeve 1204 from the sleeve proximal end opening 1308 to the sleeve distal end opening 1312. The first channel 1314 has a cartridge receiving portion 1316 and a ring receiving portion 1318.

The cartridge receiving portion 1316 extends from the sleeve proximal end opening 1308 to a first channel transition point 1320. A diameter of the cartridge receiving portion 1316 tapers substantially linearly from a first diameter, $D_1$ at the proximal end 1306 of the reinforcing sleeve 1204 to a second, smaller diameter, $D_2$ near at the first channel transition point 1320, resulting in the cartridge receiving portion 1316 having a substantially frustoconical shape. In some examples, the first diameter, $D_1$ is in a range of 7 mm to 8 mm (e.g., 7.887 mm). In some examples, the second diameter, $D_2$ is in a range of 6 mm to 7 mm (e.g., 6.04 mm).

The ring receiving portion 1318 extends from the first channel transition point 1320 to the sleeve distal end opening 1312. A diameter, $D_3$ of the ring receiving portion 1318 is greater than the second diameter, $D_2$. A shoulder 1322 is formed at the channel transition point 1320 due to an abrupt change in the diameter of the first channel 1314 from the second diameter, $D_2$ to the third diameter, $D_3$. In some examples, the third diameter, $D_3$ is in a range of 7.938 mm to 8.326 mm.

The ring receiving portion 1318 of the channel 1314 is configured to fixedly receive a ring 1324. In some examples, the ring 1324 is press fit into the ring receiving portion 1318 such that it rests against the shoulder 1322 and is substantially flush with the sleeve distal end 1306. In other examples, the ring 1324 is glued, welded, or otherwise affixed in the ring receiving portion 1318. An injection channel 1326 extends through the ring 1324 and permits ejection of injectate from the injector head assembly 1200.

In some examples, the sleeve proximal end 1306 includes threads 1328 for connecting the reinforcing sleeve 1204 to an injector mechanism (not shown). In some examples, the distal end 1310 of the reinforcing sleeve 1204 includes a flared portion 1330 for interfacing with one or more injector head accessories.

In some examples, the reinforcing sleeve 1204 is formed from a sheet metal material. In some examples, a wall 1380 adjacent to the cartridge receiving portion 1316 has a maximum thickness in the range of 0.5 mm to 5 mm and a minimum thickness in the range of 0.5 mm to 5 mm.

While specific ranges of diameters and thicknesses are provided for the reinforcing sleeve 1204, it should be noted that the diameters and thicknesses are generally configurable to accommodate a cartridge of any size, as long as the substantially frustoconically shaped cartridge receiving portion of the sleeve conforms to the cartridge.

Figure 14:
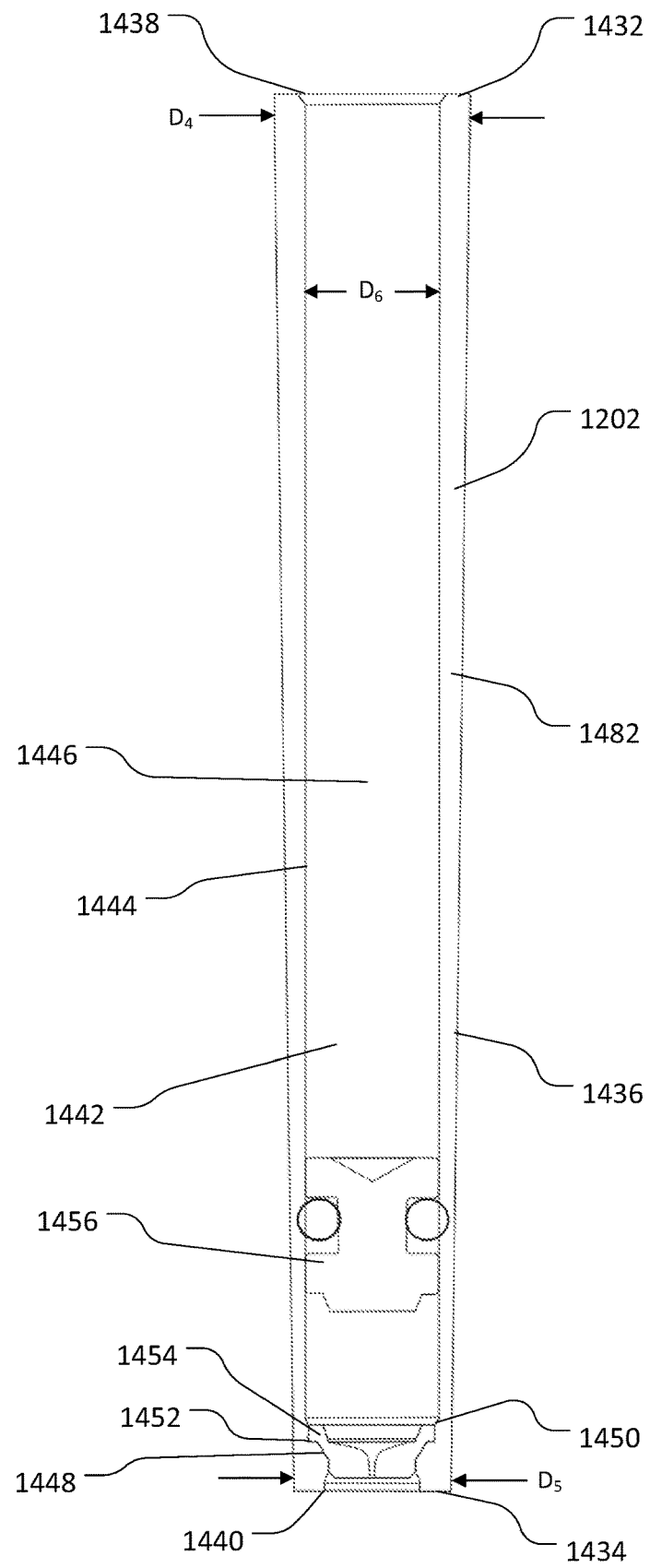
FIG. 14 is a cartridge of the fourth embodiment of FIG. 12.

Referring to FIG. 14, the cartridge 1202 is an elongate, substantially frustoconically shaped member formed as a container with relative thin plastic walls 1482. The cartridge 1202 has a cartridge proximal end 1432 and a cartridge distal end 1434. An outer surface 1436 of the cartridge 1202 extends along a length of the cartridge 1202 from the cartridge proximal end 1432 to the cartridge distal end 1434. A diameter of the outer surface 1436 of the cartridge 1202 tapers substantially linearly from a fourth diameter, $D_4$ to a fifth, smaller diameter, $D_5$, resulting the outer surface 1436 of the cartridge 1202 having a substantially frustoconical shape. In general, the fourth diameter $D_4$ is slightly larger than the first diameter, $D_1$ of the cartridge receiving portion 1316 of the first channel 1314 and the fifth diameter, D5 is slightly larger than the second diameter, D2 of the cartridge receiving portion 1316 of the first channel 1314. In some examples, the fourth diameter, $D_4$ is in a range of 7.5 mm to 8 mm. In some examples, the fifth diameter, $D_5$ is in a range of 6 mm to 6.5 mm.

The cartridge proximal end 1432 includes a cartridge proximal end opening 1438 and the cartridge distal end 1434 includes a cartridge distal end opening 1440. A second channel 1442 is defined by an inner surface 1444 of the cartridge 1202 and extends along a length of the cartridge 1202 from the cartridge proximal end opening 1438 to the cartridge distal end opening 1440. The second channel 1442 includes a plunger receiving portion 1446 (i.e., a bore) and a nozzle receiving portion 1448.

The plunger receiving portion 1446 extends from the cartridge proximal end opening 1438 to a second channel transition point 1450. The plunger receiving portion 1446 has a substantially constant, sixth diameter, $D_6$ along its length, resulting in the plunger receiving portion 1446 having a substantially cylindrical shape. In some examples, the sixth diameter, $D_6$ is in a range of 5 mm to 6 mm. In general, the sixth diameter, D6 depends on and is made to conform to the actuation system (e.g., the injector mechanism) being used.

The nozzle receiving portion 1448 extends from the second channel transition point 1450 to the cartridge distal end opening 1440. The nozzle receiving portion 1448 includes a second shoulder 1452 configured to mate with an injection nozzle 1454 such that the injection nozzle 1454 is properly seated in the nozzle receiving portion 1448 and is prevented from exiting the cartridge 1202 via the cartridge distal end opening 1440.

In FIG. 14, the injection nozzle 1454 is shown received in the nozzle receiving portion 1448. In some examples, the injection nozzle 1454 is affixed (e.g. glued or welded) in the nozzle receiving portion 1448. In some examples, the injection nozzle 1454 is integrally formed in the nozzle receiving portion 1448 (e.g., the injection nozzle 1454 is formed during injection molding of the cartridge 1202).

A plunger 1456 is disposed in the plunger receiving portion 1446 of the second channel 1442. In general, movement of the plunger 1456 along the plunger receiving portion 1446 is substantially unimpeded due to the constant sixth diameter, $D_6$ of the plunger receiving portion 1446.

In some examples, the walls 1482 of the cartridge 1202 in a region along the plunger receiving portion 1446 have a maximum thickness in the range of 0.6 mm to 1.2 mm and a minimum thickness in the range of 0.5 mm to 0.6 mm.

b. Assembly and Operation

Referring again to FIG. 12, to assemble the injector head assembly 1200, the cartridge 1202 is inserted into the cartridge receiving portion 1316 of the first channel 1314 of the reinforcing sleeve 1204. The outer surface 1436 of the cartridge 1202 has a shape corresponding to the cartridge receiving portion 1316 of the first channel 1314 such that the cartridge 1202 can be easily placed in the cartridge receiving portion 1316. However, due to the slight differences in diameters, between the outer surface 1436 of the cartridge 1202 and the cartridge receiving portion 1316, the cartridge 1202 cannot be fully inserted into the cartridge receiving portion 1316 without application of force. This is an intentional feature since forcing the cartridge 1202 into the cartridge receiving portion 1316 causes a slight compression of the cartridge 1202, ensuring that the outer surface 1436 of the cartridge 1202 is substantially uniformly supported by the inner surface 1315 of the cartridge receiving portion 1316 of the first channel 1314.

Therefore, to finalize the assembly of the injector head assembly 1200, a force is applied to the cartridge 1202 and/or the reinforcing sleeve 1204, causing the cartridge 1202 to move into the cartridge receiving portion 1316 of the first channel 1314 until the distal end 1434 of the cartridge 1202 makes contact with the first shoulder 1322 of the cartridge reinforcing sleeve 1204.

Once assembled, the injector head assembly 1200 is attached to an injector to perform an injection operation. To perform the injection operation, an actuator causes the plunger 1456 to move through the plunger receiving portion 1446 of the second channel 1442 in a direction from the proximal end 1432 of the cartridge 1202 toward the distal end 1434 of the cartridge 1202. The movement of the plunger 1456 causes an increased pressure in injectate present in the plunger receiving portion 1446 of the second channel 1442, which in turn causes ejection of injectate from the injector head assembly 1200 via the injection nozzle 1454 and the injection channel 1326.

The reinforcing sleeve 1204 substantially fully supports the cartridge and prevents deformation of the cartridge 1202 due to the pressurization of the injectate in the cartridge 1202. Furthermore, little to no compression of the relatively thin plastic walls of the cartridge occurs since a majority of force applied to the cartridge walls is transferred through the walls to the rigid reinforcing sleeve 1204.

Thus, during an injection operation, as plunger 1454 moves through the plunger receiving portion 1446 of the second channel 1442, pressure rises in the plunger receiving portion 1446. Pressure is exerted on the wall 1482 of cartridge 1202 but the reinforcing sleeve 1204 prevents the pressure from deforming wall 1482 of cartridge 1202. In some examples, the pressure also causes compression of the wall 1482 of cartridge 1202, but the compression is minimal due to thin walls. The first shoulder 1322 formed by the ring 1324 in the ring receiving portion 1318 of the first channel 1314 prevents the distal end 1434 of the cartridge 1202 from separating from the cartridge 1202 and being ejected from the reinforcing sleeve 1204.

V. Fifth Embodiment

Figure 15:
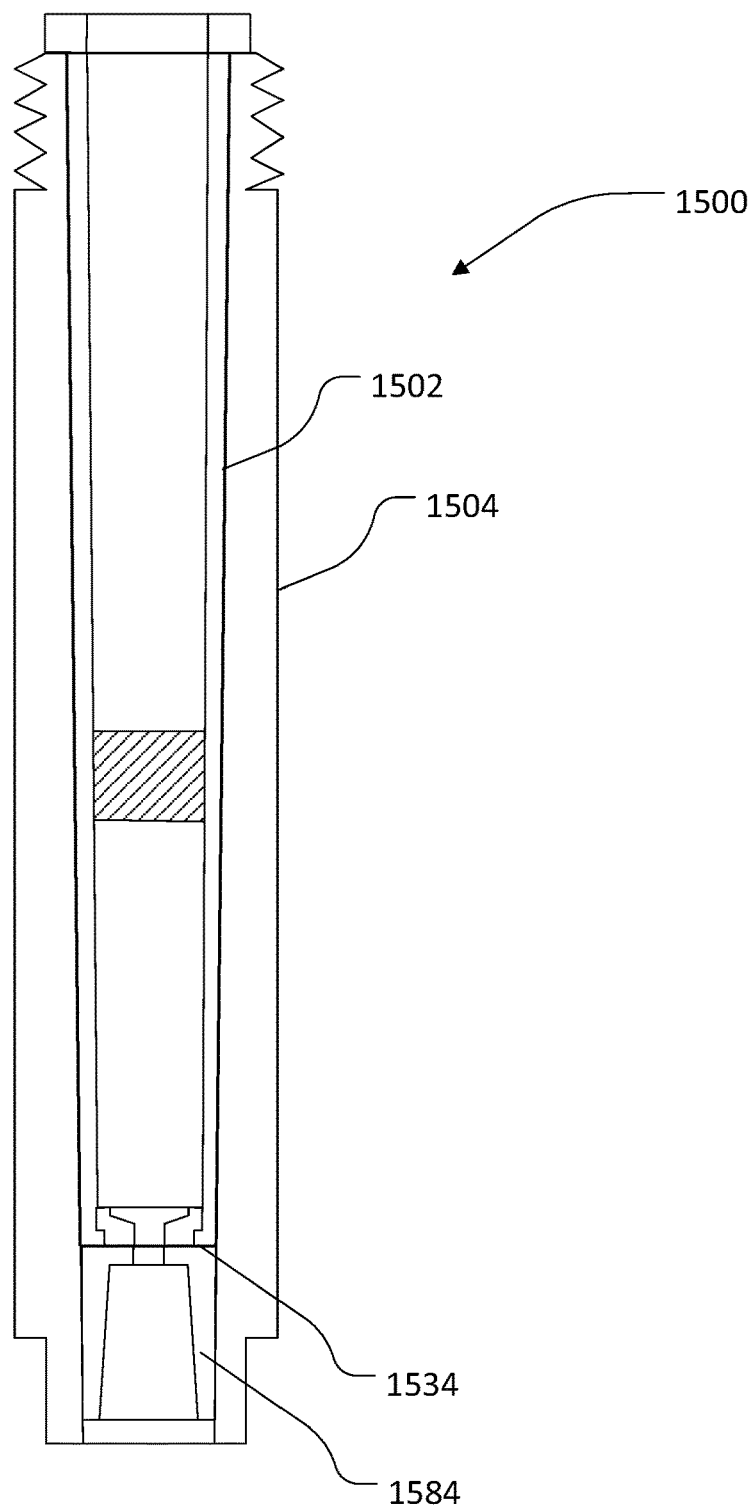
FIG. 15 is a fifth embodiment in an assembled state.

Referring to FIG. 15, in another embodiment, an injector head 1500 includes a reinforcing sleeve 1504 with a cartridge 1502 disposed therein. The injector head assembly 1500 has a similar configuration to the injector head assembly of FIG. 12. One difference however is that the cartridge 1502 of FIG. 15 has a Luer type connector 1584 disposed at its distal end 1534. The Luer connector 1584 is configured to receive a corresponding part of a syringe (not shown) for filling the cartridge 1502 with injectate.

Having described the invention, and a preferred embodiment thereof, what is claimed as new, and secured by Letters Patent is:

1. An apparatus for transdermal injection, said apparatus comprising:
   a collet configured to transition between a first state and a second states state, wherein in said first state, said collet receives a cartridge with a predetermined elongate shape, and in said second state, an inner surface of said collet substantially conforms to the predetermined elongate shape of the cartridge such that expansion of the cartridge, when the cartridge is pressurized, is substantially uniformly opposed;
   fingers configured to move along lines parallel to an axis of said collet, wherein said collet comprises a first leg and a second leg, wherein movement of said fingers causes said first leg and said second leg to pivot, thereby causing said transition, wherein said first leg and said second leg each have an inner surface that defines a recess, said recess being configured to substantially conform to the predetermined elongate shape of the cartridge, wherein, as said fingers move along said first leg and said second leg, said collet transitions into said second state;
   wherein said first leg and said second leg are configured to pivot during transition of said collet between said first state and said second state.

2. The apparatus of claim 1, wherein the predetermined elongate shape of the cartridge is substantially frustoconical and said recess is configured to accommodate a portion of the substantially frustoconical shape of the cartridge.

3. The apparatus of claim 1, further comprising pivots inserted through a distal end of each of said first leg and said second leg .

4. The apparatus of claim 1, wherein said first leg and said second leg each comprise a straight proximal section and a tapered distal section.

5. The apparatus of claim 1, wherein said first leg and said second leg are configured to drive said cartridge in a distal direction as said collet transitions from said first state to said second state.

6. The apparatus of claim 1, wherein, when said collet is in said second state, said recess of said first leg and said second leg holds an entire outer wall of said cartridge.

7. The apparatus of claim 1, wherein said fingers are constituents of a yoke.

8. The apparatus of claim 1, wherein said collet is configured such that, when said collet is in said second state, said cartridge is flush with a distal end of said collet.

9. The apparatus of claim 1 wherein a portion of the inner surface of the first leg is in contact with a portion of the inner surface of the second leg in said second state.

\* \* \* \* \*